United States Patent
Unhoch

(10) Patent No.: US 10,118,849 B2
(45) Date of Patent: Nov. 6, 2018

(54) METHOD AND KIT FOR TREATING RECREATIONAL WATER

(71) Applicant: Arch Chemicals, Inc., Atlanta, GA (US)

(72) Inventor: Michael Joseph Unhoch, Tyrone, GA (US)

(73) Assignee: Arch Chemicals, Inc., Atlanta, GA (US)

( * ) Notice: Subject to any disclaimer, the term of this patent is extended or adjusted under 35 U.S.C. 154(b) by 945 days.

(21) Appl. No.: 14/261,679

(22) Filed: Apr. 25, 2014

(65) Prior Publication Data

US 2014/0319059 A1 Oct. 30, 2014

Related U.S. Application Data

(60) Provisional application No. 61/816,369, filed on Apr. 26, 2013.

(51) Int. Cl.

| | |
|---|---|
| *A61L 2/00* | (2006.01) |
| *A61L 9/00* | (2006.01) |
| *C02F 9/00* | (2006.01) |
| *C02F 1/52* | (2006.01) |
| *C02F 1/56* | (2006.01) |
| *C02F 1/76* | (2006.01) |
| *C02F 1/00* | (2006.01) |
| *C02F 103/42* | (2006.01) |

(52) U.S. Cl.
CPC ............ *C02F 9/00* (2013.01); *A61L 2/00* (2013.01); *A61L 9/00* (2013.01); *C02F 1/004* (2013.01); *C02F 1/5245* (2013.01); *C02F 1/56* (2013.01); *C02F 1/76* (2013.01); *C02F 1/766* (2013.01); *C02F 2103/42* (2013.01); *C02F 2201/006* (2013.01); *C02F 2209/001* (2013.01); *C02F 2303/04* (2013.01); *C02F 2303/16* (2013.01); *C02F 2305/12* (2013.01)

(58) Field of Classification Search
None
See application file for complete search history.

(56) References Cited

U.S. PATENT DOCUMENTS

| | | | | |
|---|---|---|---|---|
| 3,581,895 | A | * | 6/1971 | Howard ................. B01D 24/14 210/108 |
| 5,204,452 | A | * | 4/1993 | Dingilian .............. C02F 1/5263 209/5 |
| 5,565,109 | A | | 10/1996 | Sweeny |
| 5,603,941 | A | | 2/1997 | Farina et al. |
| 5,981,461 | A | | 11/1999 | Counts et al. |
| 7,157,009 | B2 | | 1/2007 | Nichols et al. |
| 7,407,590 | B2 | | 8/2008 | Ludensky et al. |
| 8,933,244 | B2 | | 1/2015 | Janak et al. |
| 2003/0029812 | A1 | | 2/2003 | Burns et al. |
| 2003/0228373 | A1 | | 12/2003 | Ludensky et al. |
| 2005/0242043 | A1 | * | 11/2005 | Nichols .................... C02F 1/76 210/721 |
| 2009/0145857 | A1 | * | 6/2009 | Martin .................... C02F 1/722 210/754 |
| 2013/0186837 | A1 | * | 7/2013 | Somesla ................... C02F 1/54 210/719 |
| 2014/0339176 | A1 | * | 11/2014 | Mastio .................... C02F 1/685 210/749 |
| 2015/0352561 | A1 | * | 12/2015 | Holland ............... B01D 17/047 210/695 |

FOREIGN PATENT DOCUMENTS

| | | |
|---|---|---|
| EP | 0137875 A1 | 4/1985 |
| EP | 0137875 B1 | 8/1989 |
| EP | 2165981 A1 | 3/2010 |
| WO | WO2012/101051 A1 | 8/2012 |

OTHER PUBLICATIONS

Shields et al., The effect of cyanuric acid on the disinfection rate of Cryptosporidium parvum in 20-ppm free chlorine, Apr. 1, 2008, pp. 1-6.*
Lowering Swimming Pool Chlorine, Nov. 6, 2012, p. 2, 4, 5.*
Swimming Pool Water Chemistry Fact Sheet, Feb. 1, 2001, pp. 1-3.*
http://www.ncbi.nlm.nih.gov/pubmed/18957779; / Aug. 24, 2015; Abstract ; The effect of cyanuric acid on the disinfection rate of Cryptosporidium parvum in 20-ppm free chlorine; Shields et al.

* cited by examiner

*Primary Examiner* — Bobby Ramdhanie
*Assistant Examiner* — Donovan Bui-Huynh
(74) *Attorney, Agent, or Firm* — Dority & Manning, P.A.

(57) ABSTRACT

Provided herein is a method for reducing down-time in a recreational body of water having a water filtering system and water recirculation system after a potential release of *Cryptospridium* oocyst and/or *Giardia* cysts. Also described is a kit for practicing the method for reducing down-time in a recreational body of water that may have a potential release of *Cryptospridium* oocyst and/or *Giardia* cysts.

9 Claims, No Drawings

METHOD AND KIT FOR TREATING RECREATIONAL WATER

RELATED APPLICATION

The present application is based upon and claims priority to U.S. Provisional Application Ser. No. 61/816,369 filed on Apr. 26, 2013, which is incorporated herein by reference.

FIELD OF INVENTION

The present invention relates to a method and kit used to treat recreational water after a fecal release in the recreational water, in particular a fecal release which may include a release of *Cryptosporidium* and/or *Giardia*.

BACKGROUND OF THE INVENTION

The *Cryptosporidium* is a waterborne parasitic protozoan responsible for the waterborne disease Cryptosporidiosis. Outbreaks of Cryptosporidiosis have been attributed to ingestion of drinking water, recreational water or food containing viable oocysts of *Cryptosporidium*. *Cryptosporidium* oocysts are typically introduced into the water through contamination of the water with fecal matter from cattle or humans containing oocysts. The oocysts have a hard outer cell wall that renders the oocysts resistant to the effects of chlorine present at concentrations typical of drinking water and recreational water. The oocysts are approximately 4-6 microns in size, which makes them difficult to remove by filtration. Since filtration and chlorination are universally practiced as a means for clarifying and sanitizing drinking water in municipal water treatment facilities and for maintaining the clarity of recreational water such as in swimming pools, water parks, hot tubs, baths and spas, the chlorine resistance and size of the oocysts make it difficult to ensure that water is free of this disease-causing microorganism.

A variety of filters and filter systems are used to clarify water in swimming pools, water parks, hot tubs and spas. Sand filters are common for swimming pool use and municipal water treatment. Diatomaceous earth filters are also available for use in swimming pools and water parks. Cartridge filters available to both pools and spas utilize a synthetic fabric enclosed in a plastic cartridge. Different filter media exhibit different capabilities for removing particles that vary in size. Sand filters are capable of filtering out particles in the size range of 25-50 microns, while cartridge filters are typically capable of removing particles in the size range of 15-25 microns. Diatomaceous earth filters exhibit the capability of removing particles in the size range of 5-10 microns, but have to be replaced frequently.

Coagulation and flocculation followed by filtration is commonly utilized in the treatment of drinking and recreational water to remove suspended microscopic particles. Some suspended microscopic particles tend to possess an electrostatic charge that prevents the particles from aggregating into larger filterable aggregates due to charge-charge repulsion. For example, bacteria and *Cryptosporidium* oocysts have a negative surface charge. This can be often overcome through the use of coagulants and flocculants. Coagulants are chemicals, that when dissolved in water, form ions of charge opposite to that of the suspended particles.

Flocculants are typically water soluble or water dispersible high molecular weight polyelectrolyte long chain polymers composed of repeating monomeric units that can be categorized into inorganic or organic compounds. The inorganic polyelectrolytes are polymerized metal salts and may include polyaluminum hydroxychloride, polyaluminum silicate sulfate and polyaluminum sulfate. Organic polyelectrolyte flocculants are derived synthetically or obtained from natural sources. The organic polyelectrolytes can exist as charged or uncharged polymers depending on their composition. Flocculants when added to water containing aggregates of microscopic particles or non-aggregated particles exhibit the ability to bind and gather the particles or particle aggregates into even larger aggregates that can be easily filtered.

It has also been suggested to treat recreational water possibly containing *Cryptosporidium* and/or *Giardia* by hyper-chlorination of the water. Hyper-chlorination is a process in which additional free chlorine is added to the recreation water such that the water contains free chlorine at a level generally above about 10-ppm; typically in the range of about 10-50 ppm. However, hyper-chlorination alone is effective in killing these parasites, in particular in killing *Cryptosporidium* but requires long contact times in presence of cyanuric acid. Cyanuric acid is used to stabilize the free chlorine against degradation by sunlight.

These treatments have not been successful in removing *Cryptosporidium* oocysts and/or *Giardia* cysts from recreational water, but requires the pool to remain closed to swimmers sometimes for days. As such, there is a need in the art for an effective method to remove *Cryptosporidium* and/or *Giardia* from the recreational water and to remove them in a manner which is cost effective, timely and easy to manage. The present invention provides an answer to that need.

SUMMARY OF THE INVENTION

In one aspect, the present invention provides a method for reducing down-time in a recreational body of water having a water filtering system and water recirculation system after a potential release of *Cryptospridium* oocyst and/or *Giardia* cysts. The method includes adding a halogenating agent to the body of water to raise the concentration of the active halogen to a level between about 10 ppm and about 100 ppm and adding at least one agglomeration aid to the body of water at a level between 0.1 ppm and 3.0 ppm. After addition of both the halogenating agent and the agglomeration aid to the body of water, the water is then recirculated with the recirculation system through said filtering system for a period of time. After the period of time, the concentration of active halogen in the water is reduced to a level of between 1 and 9 ppm after the water has been recirculated through the filtering system for the period of time. In an additional aspect, a filtration enhancement aid may be added to the filtration system prior to recirculating the water through the filtering system.

In another aspect of the present invention, provided is a method for reducing down-time in a recreational body of water having a water filtering system and water recirculation system after a potential release of *Cryptospridium* oocyst and/or *Giardia* cysts. The method of this aspect includes adding a halogenating agent to the body of water to raise the concentration of the active halogen to a level between about 10 ppm and about 50 ppm. In addition, a filtration enhancement aid is added to the filtering system. Once the active halogen level is raised and the filtration enhancement aid is added to the filtering system, the water is then recirculated within the recirculation system through said filtering system for a period of time. After the period of time, the filtering system is backwashed to remove any captured *Cryptospridium* oocyst and/or *Giardia* cysts trapped by the filtering system. Next, the concentration of active halogen in the water is reduced to a level of between 1 and 9 ppm after the water has been recirculated through the filtering system for the period of time and the filtering system has been backwashed.

In an additional aspect of the present invention, provided is a kit for treating a potential release of *Cryptosprdium* oocyst and/or *Giardia* cysts in a recreational body of water. The said kit contains a halogenating agent, an agglomeration aid for addition into the body of water and/or a filtration enhancement aid for addition into a filter; a cyanuric acid test kit; and a chlorine neutralizing agent.

These and other aspects will become apparent when reading the detailed description of the invention.

DETAILED DESCRIPTION OF THE PREFERRED EMBODIMENTS

It has now been surprisingly found that the time period for removal of *Cryptospridium* oocyst (*Cryptosporidium parvum*) and/or *Giardia* cysts (*Giardia duodenalis*) or rendering the oocyst or cysts inactive can be greatly reduced by following the methods of the present invention in conjunction with the kit of the present invention.

In recreational water, free chlorine is generally present in an amount under 10 ppm, more typically in a 3 ppm to 6 ppm range. This level of free chlorine is sufficient to actively control most microbes in the water to safe levels for human contact with the water. However, *Cryptosporidium* oocysts and *Giardia* cysts are generally not inactivated with this level of free chlorine in recreational bodies of waters such as swimming pools, hot tubs, spas, water parks, and the like.

The first step of the methods of the present invention is to hyper-halogenate the body of water by the addition of a halogenating agent to the body of water. The term "halogenating agent" as used herein refers to compounds having a halogen atom bound to a strongly electronegative atom such as oxygen, nitrogen, or another halogen, and capable of donating a positively charged halogen atom. Representative halogenating agents include, for example, sodium hypochlorite, lithium hypochlorite, calcium hypochlorite, chlorine, hypochlorous acid, bromine, hypobromous acid, N-chlorosuccinimide, sodium hypobromite, pyridinium bromide perbromide, N-bromosuccinimide, dichlorodimethylhydantoin, bromochlorodimethylhydantoin dibromodimethylhydantoin, dichloroisocyanurate, or trichloroisocyanurate and combinations thereof. Other suitable halogenating agents will be readily apparent to those skilled in the art.

Hyper-halogenation, as used herein means a free halogen level greater than 10 ppm, and generally greater than 20 ppm. The upper limit to hyper-halogenation is not critical but is generally limited to about 100 ppm. Above about 100 ppm, the chlorine in the water may become corrosive to metal used in or around the body of water, can cause damage to plastic parts of the recirculation system, and can cause damage to pool lines or coatings applied to the pool walls. Typically, hyper-halogentation will be in the range of about 10 ppm to about 100 ppm, more typically between 10 ppm and 60 ppm, with the range of about 20 ppm to about 50 ppm being typically used. These levels of free chlorine in the water have been found to oxidize the surfaces of both *Cryptosporidium* oocysts and *Giardia* cysts over a period of time. The period of time can be several hours to several days, depending of the amount of the free chlorine and cyanuric acid in the recreational body of water.

*Cryptosporidium* oocysts and *Giardia* cysts are known to have negative charges on their surfaces. As such, at least one agglomeration aid, which are positively charged, is added to the recreational water containing or potentially containing *Cryptosporidium* oocysts and *Giardia* cysts. The agglomeration aid, with its positive charge, serves to attract the negatively charged *Cryptosporidium* oocysts and *Giardia* cysts, or serves to reduce the negative charge of the *Cryptosporidium* oocysts and *Giardia* cysts, allowing the oocyst and/or cyst to come together and agglomerate, by binding to the agglomeration aid, or by having a reduced charge and allowing the *Cryptosporidium* oocysts and *Giardia* cyst to come together forming a stabilized floc or agglomeration of the *Cryptosporidium* oocysts and *Giardia* cyst. This allows the agglomerated particles to be filtered by the filtration system. Agglomeration aids include flocculants and coagulants.

Suitable flocculants include, for example polyaluminum chloride, cationic polymers selected from the group consisting of polyamines, polyacrylamides polydiallyldimethylammonium chloride. Suitable coagulants include, for example, metal salts, such as ferric chloride; aluminum sulfate and mixtures thereof.

The agglomeration aid is generally added to the recreational water in an amount of between 0.1 ppm and 3.0 ppm. The agglomeration aid may be added continuously or it may be added as a "slug" or one-time addition. Care should be taken not to exceed the upper limit, since too much of the agglomeration aid in the recreational water may have a negative effect on agglomeration of the *Cryptosporidium* oocysts and *Giardia* cyst.

Recreational water can be associated with a recirculation system; the recirculation system generally has a pump, piping and a filtering system. Generally, the pump draws water from the recreational body of water through skimmer or drains in the pool and brings the water to the pump with piping. The pump pulls the water through the pump and into a filtration system. The filtration system is a single filter or a series of filters which are designed to remove particles from the waters. Exemplary water filtration systems include, for example, sand filters, diatomaceous earth filters or a cartridge filters.

As an alternative to the addition of an agglomeration aid, or in addition to the agglomeration aid, a filtration aid may be added to the filtration system to assist the filtration system in removing *Cryptosporidium* oocysts and *Giardia* cysts from the water being circulated through the filtration system. Suitable filtration aids include, for example, diatomaceous earth, cellulose, chitin, aluminum sulfate, perlite and mixtures thereof. In the case of sand filters, the filtration aid may be added directly to the sand filter. The filtration aid serves to coat the filtration particles, thereby assisting the filter in removing *Cryptosporidium* oocysts and *Giardia* cyst from the water, by trapping the oocyst and/or cyst in the filter.

Once the water is hyper-halogenated and the agglomeration aid and/or filtration aid is added accordingly, the recirculation system is allowed to recirculate the water through the filtration system to remove the *Cryptosporidium* oocysts and *Giardia* cyst present in the water. The period of time may vary depending size of the pool and the capacity of the recirculation system. In any event, the method of the present invention is effective in reducing the amount of time necessary to inactivate and/or remove oocyst and/or cyst from the recreation water, as compared to using just one of the methods alone. As such the method of the present invention allows the recreational water to be used with a shorter down time, meaning that the pool will be ready and safe for use in a shorter period of time. This method can be advantageous for commercial and community swimming pools that are well used by the public to effectively treat and prevent a potential outbreak of cryptosporidiosis, and the like, due to contact commercial, municipal and community recreational water facilities containing *Cryptosporidium* oocysts and *Giardia* cysts. The time reduction can be in the magnitude of 2-10 fold.

Once water has been recirculated through the filtration system for a period of time, it is necessary to remove the trapped *Cryptosporidium* oocysts and *Giardia* cysts from the filtration system. This is accomplished by "back washing" the filter by reversing the flow of water through the filter. Water that is back washed through the filter is generally sent to a drain which leads to a water treatment plant for further processing. Back washing releases the capture *Cryptosporidium* oocysts and *Giardia* cysts from the filter and from the recreational water system. In addition to back washing, the body of the recreational water should also be vacuumed to remove any particles on the floor or walls of the recreational water body.

Once the filtration system is backwashed, the free chlorine level in the recreation water must be returned to levels prior to hyper-halogenation, so that the recreational water can once again be enjoyed by users. Suitable halogen neutralizers include, for example sodium thiosulfate, sodium metabisulfite, hydrogen peroxide, etc. The free chlorine content of the recreational water should be returned to the range of about 1-10 ppm, generally between 3-6 ppm.

The time necessary to achieve inactivation and removal of *Cryptosporidium* oocysts and *Giardia* cysts form the recreational water can also be dependent on other factors, including water temperature, pH and the presence of cyanuric acid. Cyanuric acid is present in pools as a stabilizer for free chlorine. However, cyanuric acid has been found to reduce the effectiveness of hyper-halogenation on a recreational body of water against *Cryptosporidium* oocysts. As such, the method of the present invention may further include determining the cyanuric acid level in the body of water prior to adding the halogenating agent. At this point, the cyanuric acid may be neutralized, or in the alternative the amount of halogenating agent added to hyper-halogenate the body of water is based on the amount of the cyanuric acid level in the body of water. Generally, as the amount of the cyanuric acid goes up, the higher of the amount of the halogenating agent is used. Typically, the amount of halogenating agent added to the body of water is proportional to the level of the cyanuric acid in the body of water. As an alternative, a cyanuric acid neutralizer may be added to the recreational water prior to hyper-halogenation.

Also provided by the present invention is a kit for treating a potential release of *Cryptospridium* oocyst and/or *Giardia* cysts in a recreational body of water. The kit contains a halogenating agent; an agglomeration aid for addition into the body of water and/or a filtration enhancement aid for addition into a filter; a cyanuric acid test kit; and a chlorine neutralizing agent. Any of the halogenating agents, agglomeration aids, filtration enhancement aids, and chlorine neutralizing agents described above may be used.

The kit may also have instructions, a chart for specifying the amount of the halogenating agent based on the amount of the cyanuric acid. The kit may be sized for particular size of a pool in terms of volume or may be provided in incremental amounts, such as 5,000, 10,000 gallon or greater increments.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A method for treating a recreational body of water having a water filtering system and a water recirculation system after a release of *Cryptosporidium* oocyst and/or *Giardia* cysts, wherein the recreational body of water has an initial active free halogen concentration between about 1 ppm and about 8 ppm, said method comprising:
   (i) adding a halogenating agent to the recreational body of water to raise the concentration of the initial active free halogen to a level between about 10 ppm and about 100 ppm;
   (ii) adding an agglomeration aid to the recreational body of water at a level between 0.1 ppm and 3.0 ppm, adding a filtration enhancement aid to said filtering system, or adding both an agglomeration aid to the recreational body of water at a level between 0.1 ppm and 3.0 ppm and adding a filtration enhancement aid to said filtering system;
   (iii) recirculating water from the recreational body of water with said water recirculation system through said water filtering system for a period of time; and
   (iv) reducing the concentration of active free halogen to a level of between 1 and 8 ppm in order to return the concentration of active free halogen to a level prior to adding the halogenating agent.

2. The method according to claim 1, wherein the filtration enhancement aid is added to the water filtering system and the method further comprises back washing the water filtering system.

3. The method according to claim 1, wherein the agglomeration aid is added to the recreational body of water and the filtration enhancement aid is added to the water filtering system, and further comprising a step of backwashing the water filtering system.

4. The method according to claim 1, wherein the agglomeration aid comprises polyaluminum chloride; ferric chloride; cationic polymers selected from the group consisting of polyamines, polyacrylamides, polydiallyldimethylammonium chloride; aluminum sulfate and mixtures thereof.

5. The method according to claim 2, wherein the filtration enhancement aid comprises diatomaceous earth, cellulose, chitin, aluminum sulfate, perlite and mixtures thereof.

6. The method according to claim 1, wherein the halogenating agent is selected from the group consisting of sodium hypochlorite, lithium hypochlorite, calcium hypochlorite, chlorine, hypochlorous acid, bromine, hypobromous acid, N-chlorosuccinimide, sodium hypobromite, pyridinium bromide perbromide, N-bromosuccinimide, dichlorodimethylhydantoin, bromochlorodimethylhydantoin dibromodimethylhydantoin, dichloroisocyanurate, and trichloroisocyanurate.

7. The method according to claim 1, wherein step (i) comprises adding the halogenating agent in an amount to raise the concentration of the initial active free halogen to a level between about 20 ppm and about 40 ppm.

8. The method according to claim 2, wherein the filtering system comprises a sand filter, diatomaceous earth or a cartridge filter.

9. The method according to claim 1 wherein the concentration of active free halogen is reduced by adding a halogen neutralizer to the recreational body of water.

\* \* \* \* \*